United States Patent
Gilbert et al.

(10) Patent No.: US 6,494,996 B2
(45) Date of Patent: Dec. 17, 2002

(54) PROCESS FOR REMOVING WATER FROM AQUEOUS METHANOL

(75) Inventors: Benjamin A. Gilbert, Pampa, TX (US); Jeffrey R. Kirkpatrick, Pampa, TX (US); John C. McCall, Pampa, TX (US); Kenneth A. Windhorst, Portland, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/766,765

(22) Filed: Jan. 22, 2001

(65) Prior Publication Data

US 2002/0134661 A1 Sep. 26, 2002

(51) Int. Cl.[7] .......................... B01D 3/36; C07C 29/82; C07C 29/86
(52) U.S. Cl. .............................. 203/14; 203/8; 203/18; 203/49; 203/43; 203/60; 203/98; 203/DIG. 23; 568/913
(58) Field of Search .................... 203/18, 14, DIG. 23, 203/60, 98, 43, 8, 49, 91–97; 568/913; 159/16.3

(56) References Cited

U.S. PATENT DOCUMENTS

| | | | |
|---|---|---|---|
| 3,293,154 A | 12/1966 | Newton | 203/18 |
| 3,686,268 A | 8/1972 | Jobert et al. | 260/465.4 |
| 3,875,212 A | 4/1975 | Ohrui et al. | 260/486 R |
| 4,076,950 A | 2/1978 | Stewart | 560/218 |
| 5,028,735 A * | 7/1991 | Segawa et al. | 560/218 |
| 5,435,892 A * | 7/1995 | Miyazaki et al. | 568/913 |

OTHER PUBLICATIONS

Filip, S. et al Determination and Calculation of Azeotropic Composition, Inz. Chem., 3(1) 107–12(Polish) 1973.*

* cited by examiner

Primary Examiner—Virginia Manoharan
(74) Attorney, Agent, or Firm—M. Susan Spiering

(57) ABSTRACT

A process for separating water from methanol in an aqueous methanol initial mixture, including subjecting said mixture to azeotropic distillation in the presence of sufficient added methyl acrylate to form an azeotrope with most of the methanol in said initial mixture such that a substantial proportion of methanol in the initial mixture is removed as an azeotrope of methanol and methyl acrylate in the overhead vapors resulting from said distillation and a major proportion of water in said initial mixture is removed in the liquid residue of said distillation.

11 Claims, 1 Drawing Sheet

DRAWING
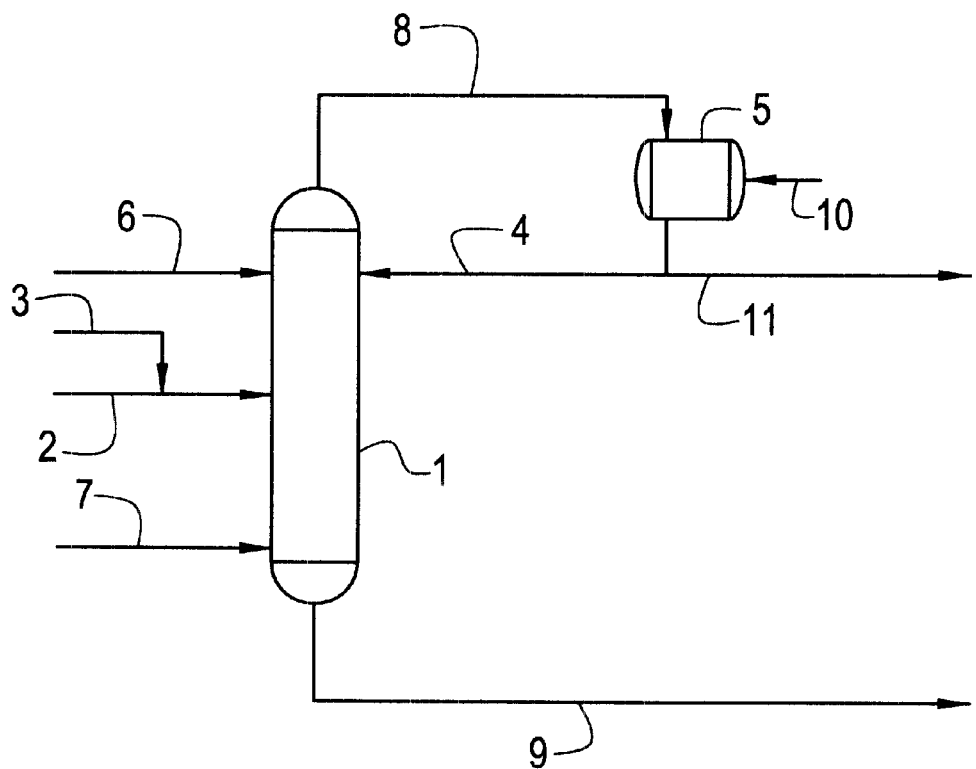

PROCESS FOR REMOVING WATER FROM AQUEOUS METHANOL

BACKGROUND OF THE INVENTION

1. Field of the Invention

This invention relates to a process for removing water from aqueous methanol by azeotropic distillation.

2. Description of the Related Art

Methanol is a widely used industrial chemical used to synthesize many different compounds and industrial products. In several processes utilizing methanol as a synthesizing feed compound, e.g., production of methyl esters, unreacted aqueous methanol is produced as a by-product which must be treated to remove water so that methanol of acceptable purity, i.e., having no more than a certain maximum percentage of water, may be recycled to the process. A common form of purification for removal of water from aqueous methanol is fractional distillation. However, disadvantages of this treatment are that the equipment for carrying out this treatment has a relatively high capital cost and the wastewater produced as a residue cannot have more than a certain proportion of methanol, e.g., about 1000 ppm, in order to meet environmental regulations. Thus, any expedient which can serve to keep the equipment and therefore its cost as small as possible, and the content of methanol in the separated water of the residue as low as possible, is very desirable.

U.S. Pat. No. 3,293,154 issued Dec. 20, 1966 to R. H. Newton, discloses a process in which a methanol-water mixture in vapor form is contacted with a water-insoluble, normally liquid hydrocarbon having a boiling point substantially no higher than the boiling point of methanol, to form an azeotrope with the free water, which azeotrope has a boiling point sufficiently different from that of methanol to accomplish the separation of enough water from the methanol to produce an essentially anhydrous alcohol.

U.S. Pat. No. 3,686,268, issued Aug. 22, 1972 to Jobert et. al., teaches a process for the manufacture of acrylic or methacrylic higher esters by transesterification of a first alcohol with an acrylic or methacrylic ester of a second alcohol having less carbon atoms than the first alcohol in the presence of a titanium phenoxide catalyst, and drawing off the second alcohol by azeotropic distillation with the ester of the second alcohol.

U.S. Pat. No. 3,875,212, issued Apr. 16, 1975 to Ohrui et. al., discloses a process for the synthesis of an acrylic ester such as methyl acrylate by esterifying acrylic acid with methanol or ethanol in the presence of a water-insoluble hydrocarbon solvent while azeotropically boiling water formed in the esterification together with the solvent and distilling the ester simultaneously; and separating the resulting effluent esterification solution into an organic solvent layer and an aqueous layer by decantation.

U.S. Pat. No. 4,076,950, issued Feb. 28, 1978 to Stewart et. al., teaches a continuous process for the preparation of acrylic and methacrylic esters such as methyl acrylate, in which substantially anhydrous product ester is added to the reactor to satisfy the ester/alkanol and ester/water azeotropes thereby removing crude product ester, unreacted alkanol and water of esterification from the esterification reactor while leaving substantially all the high boiling acrylic or methacrylic acid in the reactor.

BRIEF SUMMARY OF THE INVENTION

In accordance with this invention, water is removed from an initial mixture comprising methanol and water by subjecting said mixture to azeotropic fractional distillation in the presence of sufficient added methyl acrylate to form an azeotrope with most of the methanol in said mixture such that a substantial proportion of the methanol in the initial mixture is removed as an overhead azeotrope of methanol and methyl acrylate having an atmospheric boiling point of 62.5° C. and containing about 46 weight percent (wt. %) of methyl acrylate and about 54 wt. % of methanol, with a major proportion of the water in the initial methanol-water mixture being removed as a residue of the distillation usually containing a small amount of methanol and no more than a trace of methyl acrylate.

The process of this invention is capable of treating aqueous methanol to obtain a separated water in the residue containing substantially less methanol, and, in some cases an overhead containing significantly less water, than that obtained when no methyl acrylate is added, using similar equipment and energy expenditure, or such process can be used to treat aqueous methanol to obtain a separated water residue containing a similar amount of methanol and an overhead stream containing a comparable percentage of water, than when no methyl acrylate is added, using smaller equipment, and/or a lower expenditure of energy. Alternatively, a combination of these relative advantages may be obtained at various levels of equipment size, energy expenditure and percentage of methanol in the residue water.

It can thus be seen that the process of the invention can yield a significant economic advantage in the lower cost of equipment and/or energy and/or an environmental advantage due to a lower amount of methanol in the residue water if such water is to be discarded.

BRIEF DESCRIPTION OF THE DRAWING

The drawing is a schematic diagram of the process of this invention for separating water from a water-methanol mixture when the process is used to treat at least one recycle stream from the purification section of a process for making methyl acrylate by esterification of acrylic acid with methanol.

DETAILED DESCRIPTION OF THE INVENTION

The initial aqueous methanol mixture treated to reduce its percentage of water in accordance with this invention prior to the addition of methyl acrylate, may contain, for example, about 1 to about 99 wt. % of methanol, and about 99 to about 1 wt. % of water, preferably about 5 to about 10 wt. % of methanol and about 85 to about 95 wt. % of water, all percentages based on the weight of the total mixture. Relatively small amounts of other compounds may also be present in the initial aqueous methanol mixture, e.g., methyl acrylate, particularly if the process of separating water from methanol in accordance with this invention is employed in conjunction with methyl acrylate production, to be discussed more fully hereinafter.

The amount of methyl acrylate added to the initial aqueous methanol mixture subjected to the azeotropic distillation may be in the range, for example, of about 95% of the amount necessary to form an azeotrope with all the methanol present to about a 20% excess over the latter amount, preferably from about the approximate amount necessary to form an azeotrope with substantially all the methanol present to about a 5% excess over that amount.

Because of a low degree of solubility of methyl acrylate in water, and due to recycle streams, a small amount of methyl acrylate may be present in the initial aqueous methanol mixture subjected to azeotropic distillation under steady state conditions before the addition of methyl acrylate in the amounts described. This small amount may be larger if the azeotropic distillation process of the invention is used for the recovery and recycling of methanol in conjunction with a methyl acrylate production process, since much of the initial aqueous methanol treated is obtained in the course of recovering and recycling the portion of the excess methanol which dissolves in the water of esterification, in which the methyl acrylate product is also slightly soluble. The amount of methyl acrylate present in the initial aqueous methanol to be treated before the addition of methyl acrylate may be, for example, in the range of about 2 to about 10 wt. % based on the weight of the mixture, and this amount should be taken into account in determining how much methyl acrylate should be added to the initial aqueous methanol mixture to reach the desired amount.

The aqueous methanol mixture to be treated for the separation of water in accordance with this invention, may be added to a fractional distillation tower as a single stream or as more than one stream, e.g. different recycle streams from various purification units of a methyl acrylate production process. If more than one stream enters the tower, then the percentages of methanol, water and methyl acrylate mentioned previously apply to the total of all the streams. Furthermore, the added methyl acrylate utilized to form an azeotrope with methanol during distillation may be added to the distillation tower as a separate stream, in which case it should be added below the lowest feed point of aqueous methanol, or preferably, it may be mixed with an aqueous methanol stream before it is fed to the distillation tower.

The distillation may be carried out using a tower of any conventional design to accomplish fractionation, e.g., containing sieve trays, baffle plates, or packing. Preferably, sieve trays are utilized which may number, for example, about 5 to about 20 and some of which may be slotted. Heat may be supplied to the tower by any conventional means, e.g., injection of live steam, use of a steam heated jacket or electrical heating elements. The temperature in the tower during the separation process may be, for example, about 95 to about 100° C. near the bottom, where the residue water is withdrawn; for example, about 90 to about 95° C. at an intermediate point near where the sole or main stream of initial aqueous methanol feed mixture enters the tower; and, for example, about 60 to about 65° C. near the top of the tower from which point the methyl acrylate azeotrope vapor leaves the tower as overhead and flows to a condenser/receiver where it is condensed into a liquid mixture having a composition similar to that of the methanol/methyl acrylate azeotrope with reduced water content, the amount of water present being due to the formation of a water/methyl acrylate azeotrope having an atmospheric boiling point of 71° C. Most of the condensate is returned to the tower as reflux using a reflux ratio of, for example, about 3 to about 10, for the purpose of increasing the separation efficiency of the azeotropic distillation. That portion of the condensate not returned to the tower as reflux can be treated to separate the methanol having a substantially reduced water content from the methyl acrylate which may be recycled with makeup methyl acrylate to the azeotropic distillation. The residue from the azeotropic distillation is primarily water containing a small amount of methanol preferably no more than about 1000 ppm, more preferably no more than about 150 ppm. The residue water may be treated to recover its heat energy and reused in a related process, or it may be discarded as a waste stream.

The process of this invention employing azeotropic distillation to separate water from aqueous methanol is conveniently combined with a methyl acrylate production process of the type well known in the art wherein acrylic acid is esterified with an excess of methanol using an acid catalyst such as sulfuric acid and yielding a crude product comprising methyl acrylate, water of esterification and unreacted methanol. Pure methyl acrylate is obtained by subjecting the crude product to various purification operations including water extraction from which aqueous methanol is obtained as a residue suitable as the initial mixture to be fed to the azeotropic distillation of this invention to recover methanol having a reduced water content. Such methanol can be recycled to the methyl acrylate esterification reactor as a mixture with methyl acrylate, or after having been separated from the methyl acrylate azeotroping agent. Since the addition of water to the methyl acrylate esterification reaction tends to reverse the reaction due to equilibrium considerations, the percentage of water in the portion of the methanol/methyl acrylate overhead from the azeotropic distillation being recycled to the exterification reactor should be as low as possible, e.g., no higher than about 10 wt. %, preferably no higher than about 3wt. %.

In carrying out the process of the invention, it is desirable to add a water-soluble polymerization inhibitor, such as phenothiazine (PTZ) or hydroquinone to the system to reduce the formation of methyl acrylate polymers, too much of which causes fouling of the equipment and prevents the recovery of heat from the water residue or the reuse of such water residue due to the presence of such polymers. While the inhibitor may be injected into any stream in the system including the feed and reflux streams and the liquid in the overhead condenser-receiver, it has been found that the most benefit is obtained when the inhibitor is added only to the overhead condenser/receiver.

Turning now to the drawing, entering azeotropic distillation tower 1 are a feed stream of aqueous methanol extractive residues from the purification section of a methyl acrylate production process, fed through line 2, to which has been added methyl acrylate azeotroping agent obtained from the latter purification section, fed through line 3, a reflux stream comprising methanol, methyl acrylate and a small amount of water, fed through line 4 which is part of the liquid condensate from condenser/receiver 5, the aqueous methanol obtained as a heavy phase from a decanter (not shown) receiving the overhead condensate from the reactor/fractionating tower (not shown) of a methyl acrylate production process, fed to tower 1 through line 6, and live stream to provide heat energy and additional water to tower 1, fed through line 7. Overhead vapors from tower 1 composed primarily of the methanol/methyl acrylate azeotrope and a lesser amount of a water/methyl acrylate azeotrope are withdrawn from tower 1 and flow to condenser/receiver 5 through line 8. Water containing a small amount of methanol is withdrawn from tower 1 as a residue through line 9 and is either treated to recover its heat energy and reused in the methyl acrylate production process or is sent to waste treatment. A small amount of a polymerization inhibitor such as phenothiazine (PTZ) fed to condenser/receiver 5 through line 10, acts to reduce fouling and decrease the amount of polymer in the residue water which is desirable if the water is to be reused in the methyl acrylate process. That portion of the overhead condensate from condenser/receiver 5 not returned to tower 1 as reflux is the main product of the process of this invention and is fed through line 11 to the reactor/fractionating tower of the methyl acrylate process for reuse in the process.

The following examples further illustrate the invention.

EXAMPLE 1

For laboratory modeling of the process of the invention, an Oldershaw distillation column was employed containing a bottom reboiler section heated by an electrical element, a 10 tray section above the reboiler, a feed section above the 10 tray section, a 5 tray section above the feed section, an overhead take-off section above the 5 tray section and a condenser above the overhead take-off section. The process was started up by heating a feed comprising 9.4 wt. % of methyl acrylate, 10.47 wt. % of methanol and about 80 wt. % of water, which included added methyl acrylate in an amount of about 5% excess over that necessary to form an azeotrope with the methanol present. The feed rate was 9.2 g/min (grams per minute) the residue take off was 7.2 ml/min (milliliters per minute) and the reflux ratio was 5:1. Readings were taken of the reboiler temperature (Bottom T), temperature at the feed point (Feed T), temperature at the overhead take-off point (OH T), all in degrees Celsius, percentage of water in the overhead (OH $H_2O$, %), and parts per million of methanol in the residue (Res. MeOH, ppm). The system was assumed to be relatively stable when the residue methanol fell below 1000 ppm and the first set of readings meeting this condition was considered to be the time zero point (Time=0). Thereafter, the foregoing readings were taken at various intervals and recorded opposite the total time elapsed from the time zero point given in the following table (Time, hrs.).

TABLE

| Time, hrs. | Bottom T ° C. | Feed T ° C. | Top T ° C. | OH $H_2O$ % | Res. MeOH ppm |
|---|---|---|---|---|---|
| 0 | 97.8 | 94 | 47.7 | 2.8 | 35 |
| 0.5 | 97.8 | 92.6 | 49.6 | 5.4 | 4.8 |
| 1.0 | 97.6 | 91.7 | 54.6 | 9.9 | 22 |
| 1.5 | 97.6 | 90.5 | 50.0 | 3.0 | 26 |
| 1.75 | 97.4 | 90.3 | 49.6 | 2.5 | 33 |
| 2.5 | 97.4 | 80 | 48.8 | 2.3 | 55 |
| 3.0 | 97.5 | 77.4 | 48.6 | 3.1 | 65 |
| 3.33 | 97.4 | 80.6 | 48.5 | 2.6 | 96 |
| 4.0 | 97.5 | 72.3 | 49.0 | 3.1 | 235 |

The OH $H_2O$ and Res. readings at Time=0.5 and the OH $H_2O$ reading at Time=1.0 were probably altered by the temporary malfunction of a reflux valve affecting conditions during those intervals.

The overall values shown in the table indicate that the process of the invention is suitable for the efficient separation of water from aqueous methanol in which the residue water contains a particularly small amount of methanol, which is desirable from an environmental standpoint, while yielding an overhead condensate containing an acceptably low percentage of water. The remaining major proportion of the condensate is composed primarily of methanol and methyl acrylate in proportions close to those of the azeotrope of these compounds, and which can be separated by methods known in the art, e.g., water extraction of the methanol.

EXAMPLE 2

This example is based on the process illustrated in the drawing as described previously. Azeotropic distillation tower 1 contains 20 sieve trays, trays 6–9 of which are slotted. The aqueous methanol feed to tower 1 consists of 9.5 MLBH (thousand pounds per hour) of the extractive residues obtained from the water extraction of methanol from an overhead stream comprising methanol and methyl acrylate produced by the esterification of acrylic acid with methanol in a reactor/distillation tower, such aqueous residues being fed to tower 1 through line 2, and 1.5 MLBH of the heavy phase decanted from an overhead stream from the latter reactor/distillation tower, fed through line 6. To the feed stream in line 2 is added enough methyl acrylate to provide a 5% excess over that necessary to completely azeotrope with the methanol present, fed through line 3. The aqueous methanol and methyl acrylate fed to tower 1 through lines 2, 3 and 6 results in an overall feed comprising 8 wt. % of methanol, 6 wt. % of methyl acrylate, and 86 wt. % of water.

Also fed to tower 1 through line 7 are 6.0 MLBH of 50 psig live steam which provide heat energy. During steady state operation, tower 1 has a bottom temperature of 96° C., an intermediate temperature of 93° C. near the feed point of line 2, and a top temperature of 60° C. near the feed point of line 6. Overhead vapors in an amount of 9.0 MLBL and composed of 51 wt. % of methanol, 47 wt. % of methyl acrylate and 2 wt. % of water, leave the top of tower 1 through line 8 and are condensed in condenser/receiver 5, with 7.5 MLBH being recycled back to the top of tower 1 as reflux, and 1.5 MLBH being withdrawn through line 5 as product, for a reflux ratio of 5:1. The withdrawn product is recycled to the reactor/distillation tower of the methyl acrylate production process. A small amount of phenothiazine polymerization inhibitor is injected into condenser/receiver 5 through line 10.

Residue water in an amount of 15.0 MLBH and containing 100 ppm of methanol is withdrawn from the bottom of tower 1 through line 9 as effluent and is either treated to recover heat energy and reused as methanol extractant in the separation of methanol from methyl acrylate or is sent to waste treatment.

We claim:

1. A process for recovering methanol from an aqueous methanol mixture comprising the steps of:
   a) introducing the aqueous methanol mixture in the presence of methyl acrylate into a distillation tower having a top portion, an intermediate portion and a bottom portion, at the intermediate portion of the tower maintained at a temperature of about 90° C. to about 95° C. to form an azeotrope comprised of methanol and methyl acrylate and a residue comprised of water,
   b) removing the azeotrope as overhead vapors from the top portion of the tower at temperature of about 60° C. to about 65° C.;
   c) removing the water residue from the bottom portion of the tower at a temperature of about 95° C. to about 100° C.

2. The process of claim 1 wherein the overhead vapors are condensed to form a condensate and wherein a portion of the condensate is recycled to the distillation tower as reflux at a reflux ratio of about 3 to about 10 and wherein the remainder of the condensate is withdrawn as a product stream.

3. The process of claim 2 wherein the water content of the condensate is 10% or less.

4. The process of claim 2 wherein the water content of the condensate is 3% or less.

5. The process of claim 2 wherein at least a portion of the product stream is introduced into a process for producing methyl acrylate by esterification of acrylic acid with methanol and wherein at least a portion of the methanol in the product stream is recovered by extraction with water to form a aqueous methanol extraction.

6. The process of claim 5 wherein at least a portion of the aqueous methanol mixture is comprised of at least a portion of the aqueous methanol extraction.

7. The process of claim 2 wherein a polymerization inhibitor is added to the condensate.

8. The process of claim 7 wherein the polymerization inhibitor is phenothiazine.

9. The process of claim 1 wherein the methanol content in the water residue is 1000 ppm or less.

10. The process of claim 1 wherein the methanol content in the water residue is 150 ppm or less.

11. The process of claim 1 wherein the distillation tower is heated by injecting steam into the tower.

* * * * *